(12) United States Patent
Holme et al.

(10) Patent No.: US 6,685,916 B1
(45) Date of Patent: Feb. 3, 2004

(54) COMPOSITIONS FOR REMOVING STAINS FROM DENTAL SURFACES, AND METHODS OF MAKING AND USING THE SAME

(75) Inventors: Samantha K. Holme, Pompton Plains, NJ (US); Shiuh John Luo, Livingston, NJ (US)

(73) Assignee: Cadbury Adams USA LLC, Wilmington, DE (US)

( * ) Notice: Subject to any disclaimer, the term of this patent is extended or adjusted under 35 U.S.C. 154(b) by 0 days.

(21) Appl. No.: 10/285,217

(22) Filed: Oct. 31, 2002

(51) Int. Cl.[7] .............................. A61K 9/68; A61K 7/16; A23G 3/30; A23L 1/304
(52) U.S. Cl. ........................ 424/48; 424/435; 424/440; 424/49; 424/53; 424/57; 424/489; 424/490; 426/3; 426/4; 426/5; 426/103; 426/660
(58) Field of Search .................... 424/48, 440, 435, 424/49, 53, 57; 426/3–6, 103, 660

(56) References Cited

U.S. PATENT DOCUMENTS

| | | | | |
|---|---|---|---|---|
| 2,191,199 A | * | 2/1940 | Hall | 167/93 |
| 2,876,167 A | * | 3/1959 | Manahan | 167/93 |
| 3,004,897 A | * | 10/1961 | Shore | 167/93 |
| 3,124,459 A | * | 3/1964 | Erwin | 99/1 |
| 3,475,533 A | * | 10/1969 | Mayrand | 404/57 |
| 3,677,771 A | * | 7/1972 | Kocar | 99/134 |
| 4,037,000 A | * | 7/1977 | Burge et al. | 426/572 |
| 4,822,599 A | * | 4/1989 | Mitra | 424/57 |
| 4,923,684 A | * | 5/1990 | Ibrahim et al. | 424/52 |
| 4,985,236 A | * | 1/1991 | Ibrahim et al. | 424/52 |
| 5,096,701 A | * | 3/1992 | White et al. | 424/52 |
| 5,176,900 A | * | 1/1993 | White et al. | 424/52 |
| 5,912,007 A | * | 6/1999 | Pan et al. | 424/440 |
| 6,190,644 B1 | * | 2/2001 | McClanahan et al. | 424/52 |
| 6,379,654 B1 | * | 4/2002 | Gebreselassie et al. | 424/49 |
| 6,416,744 B1 | * | 7/2002 | Robinson et al. | 424/48 |
| 6,471,945 B2 | * | 10/2002 | Luo et al. | 424/48 |
| 6,475,469 B1 | * | 11/2002 | Montgomery | 424/49 |
| 6,479,071 B2 | * | 11/2002 | Holme et al. | 424/440 |
| 6,485,739 B2 | * | 11/2002 | Luo et al. | 424/48 |

* cited by examiner

*Primary Examiner*—Shep K. Rose
(74) *Attorney, Agent, or Firm*—Watov & Kipnes, P.C.

(57) ABSTRACT

A composition for removing stains from dental surfaces comprising a stain removing effective amount of at least two active components selected from a peroxide compound, a polyphosphate, and an anionic surfactant, in combination with an orally acceptable carrier. The present invention is further directed to methods of making and using the same.

31 Claims, 3 Drawing Sheets

COMPOSITIONS FOR REMOVING STAINS FROM DENTAL SURFACES, AND METHODS OF MAKING AND USING THE SAME

FIELD OF THE INVENTION

The present invention is related generally to stain removing compositions for promoting dental hygiene, more particularly to dental stain removing compositions containing a novel combination of stain removing agents and methods of making and using such compositions.

BACKGROUND OF THE INVENTION

Unblemished white teeth have long been considered cosmetically desirable. Unfortunately, in the absence of thorough dental cleaning, teeth can become discolored or stained from chromogenic (color-causing) substances present in food, beverages, tobacco, and the like, and internal sources such as blood, amalgam-based fillings, and antibiotics (e.g., tetracycline). The tooth structures that are generally responsible for presenting a stained appearance are enamel, dentin, and the acquired pellicle. Tooth enamel is predominantly formed from inorganic material, mostly in the form of hydroxyapatite crystals, and further contains approximately 5% organic material primarily in the form of collagen. In contrast, dentin is composed of about 20% protein including collagen, the balance consisting of inorganic material, predominantly hydroxyapatite crystals, similar to that found in enamel. The acquired pellicle is a proteinaceous layer present on the surface of tooth enamel which reforms rapidly after an intensive tooth cleaning.

Discoloration of teeth can result from extrinsic and/or intrinsic staining. Extrinsic staining of the acquired pellicle arises as a result of compounds such as tannins and other polyphenolic compounds that have become trapped in and tightly bound to the proteinaceous layer on the surface of teeth. Discoloration from this type of staining can usually be removed by mechanical methods of tooth cleaning. In contrast, intrinsic staining occurs when staining compounds penetrate the enamel and even the dentin, or alternatively, such staining arises from sources within the tooth. Discoloration from intrinsic staining is not readily amenable to mechanical methods of tooth cleaning. Chemical methods, which utilize substances that can penetrate into the tooth structure, are usually required to eliminate such discoloration. Accordingly, intrinsic tooth staining is generally more intractable and difficult to address than extrinsic tooth staining.

Currently, there are a number of basic methods for removing stains in teeth. These methods are generally based on the use of abrasives, hydrolytic agents or oxidizing agents to break down the staining material. The first method involves mechanically abrading the stain through the use of harsh abrasives or polishing agents normally employed in toothpaste preparations. Typical preparations containing abrasives are toothpastes, gels or powder dentifrices, which require close contact with the teeth. Brushing and similar scrubbing or polishing action is typically required as a complement to successful stain removal. In the second method, hydrolytic agents including proteolytic enzymes can be used to whiten teeth. These products are usually in the form of pastes or gels, and function to whiten teeth by removing the plaque and calculus that have entrapped the stain.

Oxidizing agents such as urea peroxide, hydrogen peroxide or calcium peroxide, represent the most common forms of whitening agents for tooth enamels. It is believed that peroxides whiten teeth by releasing hydroxyl radicals capable of breaking down the plaque/stain complex into a form that can be flushed away or removed by an abrasive. Treatments using oxidizing agents typically require significant time to achieve good results depending on the peroxide source and its concentration.

Other active stain removing components including surface active agents such as anionic surfactants (see U.S. Pat. Nos. 6,485,739; 6,471,945; and 6,479,071), and chelators such as polyphosphates have been incorporated into stain removing compositions because of their good stain removing properties. However, such components have a few drawbacks. For example, excess amounts of surfactants can produce an undesirable soapy taste in the composition. Chelators also provide good stain removal activity, however, if added in excess amounts, can also negatively affect the taste (e.g., salty, bitter, and metallic) of the composition. Accordingly, although chelators and surfactants are good stain removing agents, the amounts that can be added to the composition are limited to avoid or minimize the problems discussed above.

It would therefore be a significant advance in the art of dental whitening to provide a composition capable of removing stains from dental surfaces, while maintaining desirable organoleptic and taste properties. It would be a further advance to provide a composition, which may be administered to a warm-blooded animal including humans through a convenient vehicle at any time. It would be a further advance in the art to employ chewing gums and confectionery compositions as an effective vehicle for delivering stain removing agents to the teeth because they permit protracted contact of the stain removing agents to the teeth with minimal effort on the part of the warm-blooded animal and are convenient for the warm-blooded animal to use at any time.

BRIEF DESCRIPTION OF THE DRAWINGS

The following drawings are illustrative of embodiments of the present invention and are not intended to limit the invention as encompassed by the claims forming part of the application.

SUMMARY OF THE INVENTION

The present invention is generally directed to a composition for removing stains from dental surfaces in which a combination of stain removing agents have been incorporated therein so that an effective amount is available to produce an improved, synergistic stain removing or tooth whitening effect. The composition of the present invention includes a novel combination of stain removing agents that exhibits improved stain removing efficacy as compared to the use of individual stain removing agents alone, thereby enabling reduction in the effective amounts of each component incorporated. In addition, the compositions of the present invention are compatible for use in solid oral formulations including chewing gum and confectioneries, while effectively maintaining desirable organoleptic and taste properties.

In a particular aspect of the present invention, there is provided a composition for removing stains from dental surfaces, comprising a stain removing effective amount of at least two active components selected from a peroxide compound, a polyphosphate, and an anionic surfactant. The composition of the present invention will also typically contain an orally acceptable carrier.

In another particular aspect of the present invention, there is provided a method of removing stains from dental surfaces, comprising administering a stain removing effective amount of the composition of the present invention to the oral cavity of a warm-blooded animal including humans for cleaning and whitening contact with the dental surfaces thereof.

In a preferred embodiment of the present invention, the preferred peroxide compound is selected from the group consisting of carbamide peroxide, hydrogen peroxide, calcium peroxide and mixtures thereof, the preferred polyphosphate is selected from the group consisting of tripolyphosphates, tetrapolyphosphates, pyrophosphates, hexametaphosphates and mixtures thereof, and the preferred anionic surfactant is selected from the group consisting of medium and long chain fatty acid esters and salts, organic acid esters of monoglycerides and diglycerides, citric acid ester of mono- and diglycerides, lactic acid esters of mono- and diglycerides, sodium palmitate, sodium stearate, and mixtures thereof.

DETAILED DESCRIPTION OF THE INVENTION

The present invention is directed to compositions with stain removing properties for producing a whitening effect on dental surfaces that are treated with the same. Such compositions are especially suitable for removing stains, which adhere to, or are entrapped in materials on, the surface of teeth and for preventing build-up of the stain entrapping material and stains on dental surfaces. The compositions of the present invention are meant to include products, which are not intentionally swallowed for purposes of systemic administration of therapeutic agents, but are retained in the oral cavity for a sufficient time to contact the dental surfaces for purposes of providing beneficial dental effects. The compositions of the present invention may be in a form selected from, for example, dentifrices including mouthwashes, toothpastes, tooth powders, dental creams, dental flosses, liquids, gels, and the like; chewing gums including centerfilled gums, and the like; and confectioneries including mints, lozenges, and the like. In a preferred embodiment, the compositions of the present invention are in the form of chewing gums and confectionery formulations.

In accordance with the present invention, a stain removing effective amount of stain removing agents including a novel combination of at least two active components selected from peroxide compounds, polyphosphates and anionic surfactants, is employed in the compositions of the present invention to provide effective stain removing activity. Applicants have discovered that the novel combination of stain removing agents significantly improves stain removing activity over the activity of the individual component stain removing agents alone. In addition, Applicants have also discovered that the novel combination of stain removing agents enables reduction of the amount of each of the stain removing agents in the composition. Accordingly, the amount of anionic surfactants including sodium stearate, can be effectively reduced to avoid the problems associated prior art gum compositions including unpleasant mouthfeel, premature breakdown of gum base, soapy taste and the like. Applicants have further discovered that this novel combination effectively enables a reduction in the amount of polyphosphates while maintaining robust stain removing activity, thereby eliminating or significantly reducing the unpleasant taste (i.e., salty, bitter, metallic) typically associated with compositions containing higher levels of polyphosphates.

The term "stain removing effective amount" as used herein is an amount of the combination of stain removing agents disclosed herein that is sufficient to prevent, eliminate or at least reduce the presence of stains on dental surfaces in warm-blooded animals including humans, but low enough to avoid any undesirable side effects. The stain removing effective amount of the combination of stain removing agents of the present invention may vary with the type and extent of the particular stain, the age and physical condition of the warm-blooded animal including humans being treated, the duration of treatment, the nature of concurrent therapy, the specific form (i.e., salt) of the stain removing agent employed, and the particular carrier from which the stain removing agent is applied.

The concentration of the stain removing agents in the composition of the present invention depends on the type of composition (e.g., toothpaste, mouthwash and rinse, lozenge, chewing gum, confectionery, and the like) used to apply the stain removing agents to the dental surfaces, due to differences in the efficiency of the compositions contacting the teeth and due also to the effective amount of the composition generally used. The concentration may also depend on the level of the stains present.

Except as otherwise noted, the amount of the ingredients incorporated into the compositions according to the present invention is designated as % by weight based on the total weight of the composition.

In accordance with the present invention, suitable peroxide compounds include any compounds containing an O—O bond, which can break down to supply at least one active specie. Examples of preferred peroxide compounds are inorganic peroxides such as hydrogen peroxide, sodium peroxide, calcium peroxide, strontium peroxide, zinc peroxide or magnesium peroxide, and organic peroxides including, but not limited to, carbamide peroxide. The amount of the peroxide compound incorporated into the present composition will vary depending upon the particular individual or combinations of stain removing agents employed, and the type of other components or ingredients of the composition and their respective amounts. The peroxide compound of the present invention may be present in a stain removing effective amount of from about 0.01% to 10%, preferably from about 0.1% to 5%, and more preferably from about 0.2% to 3% by weight based on the total weight of the composition.

In one embodiment of the present invention, the peroxide compound may be encapsulated to prevent premature degradation and to control the release rate of the active specie from the composition of the present invention. Processes for embedding or encapsulating peroxide compounds such as through microencapsulation to yield small beads of peroxide compounds, are generally known in the art. The peroxide compound may be encapsulated in encapsulating substances including, but not limited to, edible natural or synthetic gums such as xanthan gum or guar gum; edible oils such as peanut oil, coconut oil, palm oil, or safflower oil; polymers such as gelatin, starches, polyamides, polyurethanes, or ethylcellulose; olefin copolymers such as carbowax; resins; waxes such as paraffin; mineral oils or other edible inert carriers capable of coating and preserving the peroxide compound until release such as through mechanical action (e.g. chewing) between the teeth or by enzymatic action especially interaction of the peroxide compound and saliva or water in the mouth for generating nascent oxygen. Further details on processes for encapsulating active ingredients including microencapsulation, may be found in U.S. Pat. Nos. 4,867,902, 5,403,578, 5,976,507 and 6,258,343, the contents of which are incorporated herein by reference.

In accordance with the present invention, suitable polyphosphates include any compounds having two or more phosphate groups arranged primarily in a linear configuration, although some cyclic derivatives may be present. In a preferred embodiment, the polyphosphates are those having four or more phosphate groups. Examples of preferred polyphosphates are inorganic polyphosphate salts including tripolyphosphates such as, for example, wholly or partially neutralized water soluble alkali metal salts thereof including sodium, potassium or ammonium tripolyphosphates; tetrapolyphosphates; hexametaphosphates such as sodium hexametaphosphate; pyrophosphates such as tetrasodium pyrophosphate and sodium acid pyrophosphate; and mixtures thereof. Most preferred polyphosphates are those having relatively small molecular sizes such as sodium tripolyphosphate, which typically are more soluble and exhibit enhanced penetration of plaque or biofilm to provide greater tooth whitening effect.

The amount of the polyphosphate incorporated into the present composition will vary depending upon the particular individual or combinations of stain removing agents employed, and the type of other components of the composition and their respective amounts. The polyphosphate may be present in the compositions of the present invention in a stain removing effective amount of from about 0.01% to 5.0% by weight based on the total weight of the composition. The preferred stain removing effective amount of the polyphosphate is from about 0.1% to 3.0% by weight, and the most preferred effective amount ranging from about 1.0% to 3.0% by weight.

In accordance with the present invention, suitable anionic surfactants employed in the present invention include sulfated butyl oleate, medium and long chain fatty acid esters and salts, in particular the sodium and potassium salts of the stearate and palmitate and mixtures thereof, and methyl and ethyl esters thereof, sodium oleate, salts of fumaric acid, potassium glomate, organic acid esters of mono- and diglycerides such as stearyl monoglyceridyl citrate, succistearin, dioctyl sodium sulfosuccinate, glycerol tristearate, lecithin, hydroxylated lecithin, sodium lauryl sulfate, acetylated monoglycerides, succinylated monoglycerides, monoglyceride citrate, ethoxylated mono- and diglycerides, sorbitan monostearate, calcium stearyl-2-lactylate, sodium stearyl lactylate, lactylated fatty acid esters of glycerol and propylene glycerol, glycerol-lactoesters of $C_8$–$C_{24}$ fatty acids, preferably glycerol-lactoesters of $C_{14}$–$C_{20}$ fatty acids, polyglycerol esters of $C_8$–$C_{24}$ fatty acids, preferably polyglycerol esters of $C_{14}$–$C_{20}$ fatty acids, propylene glycol alginate, sucrose $C_8$–$C_{24}$ fatty acid esters, preferably sucrose $C_{14}$–$C_{20}$ fatty acid esters, diacetyl tartaric or citric acid esters of mono- and diglycerides, triacetin and the like and mixtures thereof.

In one preferred form of the present invention, the anionic surfactants are selected from sodium stearate and sodium palmitate and mixtures thereof, sodium oleate, a mixture of citric acid esters or lactic acid esters of monoglycerides and diglycerides, as for example, glycerol stearate lactate, glycerol stearate and glycerol lactate and mixtures thereof, sucrose monostearate, sucrose distearate, sucrose monolaurate, sucrose dilaurate, polyglycerol esters of monostearate, polyglycerol esters of monolaurate and mixtures thereof.

Exemplary preferred anionic surfactants for use in the compositions of the present invention are sodium stearate, usually available as an approximate 50/50 mixture with sodium palmitate, and, a mixture of at least one citric acid ester of mono- and/or diglycerides. A suitable example of a commercial stain removing agent in the latter class is IMWITOR 370® available from Condea Vista Company. Also preferred are surfactants selected from lactic acid esters of monoglycerides and diglycerides, and mixtures thereof.

The amount of the anionic surfactant incorporated into the compositions of the present invention will vary depending upon the particular individual or combinations of stain removing agents employed, and the type of other components of the composition and their respective amounts. For example, a preferred stain removing effective amount of sodium stearate is about 0.5% by weight, a preferred amount of a mixture of lactic acid esters of monoglycerides and diglycerides is about 0.6% by weight while a preferred amount of a mixture of citric acid esters of mono- and diglycerides (e.g., IMWITOR 370®) is from about 0.6% to 1.0% by weight.

The amount of the anionic surfactant for chewing gum compositions is typically from about 0.1% to 2.0% by weight based on the total weight of the chewing gum composition. The preferred amount of the anionic surfactant is from about 0.4% to 1.2% by weight. The amount of the anionic surfactant will vary depending upon the particular carrier, and individual or combination of stain-removing agents of the present invention employed.

Some of the preferred anionic surfactants for use in the confectionery compositions of the present invention are sodium stearate, sodium palmitate and mixtures thereof. As previously indicated, sodium stearate is usually available as an approximately evenly divided mixture with sodium palmitate.

The amount of the anionic surfactants, which may be employed in the confectionery compositions of the present invention will vary over a range depending on, for example, the type of composition and the particular individual or combination of stain removing agents which are employed. Generally, the amount of stain removing agent used in the confectionery compositions of the present invention will exceed the amount of the stain removing agent employed for the chewing gum composition for a particular stain removing agent.

Typically, the anionic surfactant for the confectionery compositions will be present in an amount of from about 0.1% to 20% by weight based on the total weight of the composition. The preferred amount of the anionic surfactant is from about 3% to 15% by weight.

Typically, the anionic surfactant for other compositions including dentifrices will be present in an amount of from about 0.01% to 20% by weight based on the total weight of the composition. The preferred amount of the anionic surfactant is from about 3% to 15% by weight.

In one preferred embodiment of the present invention, the composition comprises a stain removing effective amount of the combination of sodium tripolyphosphate, sodium stearate and optionally carbamide peroxide, and an orally acceptable carrier.

The compositions of the present invention further comprise an orally acceptable carrier, in an amount appropriate to accommodate the other components of the formulation. The term "orally acceptable carrier" refers to a vehicle capable of being mixed with the active components for delivery to the oral cavity for tooth whitening and cleaning purposes, and which will not cause harm to warm-blooded animals including humans. The orally acceptable carriers further include those components of the composition that are capable of being commingled without interaction in a manner which would substantially reduce the composition's stability and/or efficacy for dental stain removal in the oral cavity in warm-blooded animals including humans, in accordance with the compositions and methods of the present invention.

The orally acceptable carriers of the present compositions can include one or more compatible solid or liquid filler diluents or encapasulating substances, which are suitable for oral administration. The carriers or excipients of the present invention may be in any form appropriate to the mode of delivery, for example, solutions, colloidal dispersions, emulsions, suspensions, rinses, gels, foams, powders, solids, and the like, and can include conventional components of toothpastes (including gels), mouthwashes and rinses, mouth sprays, chewing gums, lozenges, and confectioneries. Carriers suitable for the preparation of compositions of the present invention are well known in the art. Their selection will depend on secondary considerations like taste, cost, shelf stability and the like.

Types of additives or ingredients, which may also be included in the present compositions of the present invention, include, for example, abrasives, fluoride ion releasing compounds, thickening agents, humectants, flavoring and sweetening agents, anticalculus agents, alkali metal bicarbonate salts, surfactants, remineralizers and other miscellaneous additives such as anti-inflammatory agents, and the like. Suitable remineralizers include, for example, calcium phosphate salts such as alpha-tricalcium phosphate, monocalcium phosphate monohydrate, anhydrous dicalcium phosphate, dicalcium phosphate dihydrate, octacalcium phosphate or tetracalcium phosphate; and calcium glycerophosphate, and mixtures thereof.

The dentifrice compositions of the present invention may further include mouthwashes, rinses, and mouth sprays. Components of such mouthwashes, rinses and mouth sprays typically include water being present in an amount of from about 45% to 95%, and one or more of ethanol in an amount up to about 70%, a humectant in an amount up to about 50%, a surfactant in an amount from about 0.01% to 7%, a flavoring agent in an amount from about 0.04% to 2%, a sweetening agent in an amount from about 0.1% to 3%, and a coloring agent in an amount from about 0.001% to 0.5%. Such mouthwashes, rinses and mouth sprays may also include one or more of an anticaries agent in an amount from about 0.05% to 0.3% (e.g., fluoride ion releasing compound), and an anticalculus agent in an amount from about 0.1% to 3%.

Other dentifrice compositions of the present invention may include dental solutions. Components of such dental solutions generally include water in an amount from about 90% to 99%, and one or more of a preservative in an amount from about 0.01% to 0.5%, a thickening agent in an amount up to about 5%, and a flavoring agent in an amount from about 0.1% to 3%.

Other dentifrice compositions of the present invention may be in the form of toothpastes, tooth gels, and tooth powders. Components of such toothpastes and tooth gels generally include one or more of a dental abrasive, generally in an amount of from about 10% to 50%, a surfactant in an amount from about 0.5% to 10%, a thickening agent in an amount from about 0.1% to 5%, a humectant in an amount from about 10% to 55%, a flavoring agent in an amount from about 0.04% to 2%, a sweetening agent in an amount from about 0.1% to 3%, a coloring agent in an amount from about 0.01% to 0.5%, and water in an amount from about 2% to 45%. Such toothpastes or tooth gels may also include one or more anticaries agents in an amount from about 0.05% to 0.3% (e.g., fluoride ion releasing compound), and an anticalculus agent in an amount from about 0.1% to 13%. The liquids and solids of such compositions are proportioned to form a creamy or gelled mass, which can be extruded from a pressurized container or from a collapsible tube. Tooth powders, of course, contain substantially all non-liquid components.

Most preferred compositions of the present invention are chewing gum and confectioneries. Chewing gum compositions typically include one or more of gum bases, flavoring agent and bulk sweeteners. The term "confectioneries" as used herein includes, but is not limited to: nougats, candies, panning goods, gel confections, fondants, lozenges, hard boiled candies, mints, troches, pastilles, microcapsules, and fast-dissolving solid forms including freeze dried forms (cakes, wafers, thin films, and tablets) and fast dissolving solid forms including compressed tablets. The term "fast dissolving solid form" as used herein means that the solid dosage form dissolves in less than about 60 seconds, preferably less than about 15 seconds, more preferably less than about 5 seconds, in the oral cavity. Lozenges include discoid shaped solids comprising a therapeutic agent in a flavored base. The base may be a hard sugar candy, glycerinated gelatin, or combination of sugar with sufficient mucilage to give it form. Lozenge compositions (compressed tablet type) typically include one or more fillers (compressible sugar), flavoring agents and lubricants.

Applicants have determined that effective stain removing chewing gum and confectionery compositions can be prepared by a suitable selection of the combination of stain removing agents of the present invention and the formulation of the gum and confectionery compositions and the manner in which the combination of stain removing agents are added to the compositions which enables the release of the combination of stain removing agents in an effective amount so that the combination may come into contact with dental surfaces including tooth surfaces while maintaining or improving the organoleptic properties commonly associated with such products.

The chewing gum compositions of the present invention, may be coated or uncoated and be in the form or slabs, sticks, pellets, balls and the like. The composition of the different forms of the chewing gum compositions will be similar but may vary with regard to the ratio of the ingredients. For example, coated gum compositions may contain a lower percentage of softeners. Pellets and balls have a small chewing gum core, which is then coated with either a sugar solution or a sugarless solution to create a hard shell. Slabs and sticks are usually formulated to be softer in texture than the chewing gum core. For practice of the present invention however, in order to overcome any detrimental softening effect the surfactant active may have on the gum base, it is preferred to formulate a slab or stick gum having a firmer texture (i.e. with less softener than is typically employed).

Centerfilled gum is another common gum form. The gum portion has a similar composition and mode of manufacture to that described above. However, the centerfill is typically an aqueous solution or gel, which is injected into the center of the gum during processing. The combination of stain removing agents could optionally be incorporated into the centerfill during manufacture of the fill or into the chewing gum. The centerfill gum may also be optionally coated and may be prepared in various forms such as in the form of a lollipop.

For practice of the present invention it is preferred to use a coated gum wherein the combination of stain removing agents is in at least one of the core and the coating. Most preferred for removing stains is a coated gum wherein the combination of the stain removing agents is at least in the coating.

The chewing gum composition of the present invention includes gum base and most of the other typical chewing gum composition components such as sweeteners, softeners, flavoring agents and the like. The combination of stain removing agents employed in the present invention, includes a mixture of at least two stain removing components selected from peroxides, polyphosphates and anionic surfactants. The chewing gum composition may contain a reduced amount of softening agents such as lecithin or glycerin or may eliminate softeners. In addition, the chewing gum composition may contain a larger amount of sugar alcohols than conventional chewing gum compositions to facilitate delivery of the combination of stain removing agents employed in the present invention to the tooth surfaces.

In accordance with one aspect of the chewing gum composition of the present invention, the stain removing agents are added during the manufacture of the chewing gum composition, that is, with the sweeteners, flavoring agents and the like. In another aspect of the present invention, the stain removing agents are added as one of the last steps, preferably the last step in the formation of the chewing gum composition. Applicants have determined that this process modification incorporates the combination of stain removing agents into the gum composition without materially binding the stain removing agents therein such as may occur if the stain removing agents are mixed directly with the gum base. Thus, the stain removing agents, while only loosely contained within the gum composition can be more effectively released therefrom during a typical chewing operation. Thus, a material portion of the stain removing agents is free of the gum base.

In a further aspect of the invention, the gum base generally comprises elastomers, elastomer plasticizers, waxes, fats, oils, emulsifiers, fillers, texturizers and may include a desirable combination of the stain removing agents as hereinafter described.

Elastomers constitute from about 5% to 95% by weight of the base, preferably 10% to 70% by weight and most preferably 15% to 45% by weight. Examples of elastomers include synthetic elastomers such as polyisobutylene, polybutylene, isobutylene-isoprene co-polymers, styrene-butadiene co-polymers, polyvinylacetate and the like. Elastomers may also include natural elastomers such as natural rubber as well as natural gums such as jelutong, lechi caspi, perillo, massaranduba balata, chicle, gutta hang kang or mixtures thereof. Other elastomers are known to those of ordinary skill in the art.

Elastomer plasticizers modify the firmness of the finished gum when used in the gum base. Elastomer plasticizers are typically present in an amount of up to about 75% by weight of the gum base, preferably from about 5% to 45% by weight and more preferably from about 10% to 30% by weight. Examples of elastomer plasticizers include natural rosin esters such as glycerol ester of partially hydrogenated rosin, glycerol ester of tall oil rosin, pentaerythritol esters of partially hydrogenated rosin, methyl and partially hydrogenated methyl esters of rosin, and the like. Synthetic elastomer plasticizers such as terpene resins may also be employed in gum base composition.

Waxes include synthetic and naturally occurring waxes such as polyethylene, bees wax, carnauba and the like. Petroleum waxes such paraffin may also be used. The waxes may be present in the amount of up to about 30% by weight of the gum base. Waxes aid in the curing of the finished gum and help improve the release of flavor and may extend the shelf life of the product.

Fillers modify the texture of the gum base and aid processing. Examples of such fillers include magnesium and aluminum silicates, clay, alumina, talc, titanium oxide, cellulose polymers, and the like. Fillers are typically present in an amount of from 1% to 60% by weight.

Examples of softeners used in the gum base include hydrogenated and partially hydrogenated vegetable oils, cocoa butter, glycerol monostearate, glycerol triacetate, di- and triglycerides, fatty acids such as stearic acid, palmitic acid, oleic acid, linoleic acid, linolenic acid and the like.

The gum base constitutes between 5% and 95% by weight of the chewing gum composition, more typically 10% to 50% by weight, and most typically from about 25% to 35% by weight of the chewing gum. A higher amount of gum base is preferred.

Other ingredients used in chewing gum compositions include sweeteners, both natural and artificial and both sugar and sugarless. Sweeteners are typically present in the chewing gum compositions in amounts of from about 20% to 80% by weight, preferably from about 30% to 60% by weight. Sugarless sweeteners include, but are not limited sugar alcohols such as sorbitol, mannitol, xylitol, hydrogenated starch hydrolysates, maltitol and the like may also be present. High intensity sweeteners such as sucralose, aspartame, neotame, salts of acesulfame, and the like are typically present up to about 1.0% by weight.

Flavoring agents, which can vary over a wide range, may be selected in amounts from about 0.1% to 10.0% by weight, preferably from about 0.5% to 5.0% by weight. Flavoring agents for use in chewing gum compositions are well known and include citrus oils, peppermint oil, spearmint oil, oil of wintergreen, menthol and the like.

Softeners may be present to modify the texture of the chewing gum composition. Unlike typical gum compositions, softeners in the compositions of the present invention are typically present in reduced amounts of from about 0.5% to 10% by weight based on the total weight of the chewing gum composition.

Other materials, which may be present in the gum composition of the present invention, include antioxidants (e.g. butylated hydroxyanisole, butylated hydroxytoluene, beta-carotenes, tocopherols), colorants, flavoring agents and the like.

Coating techniques for applying a coating for a chewing gum composition such as pan and spray coating are well known. Preferred in the practice of the present invention is coating with solutions adapted to build a hard candy layer. Both sugar and sugar alcohols may be used for this purpose together with high intensity sweeteners, colorants, flavoring agents, binders and other conventional additives. When the combination of stain removing agents is provided in the coating of a chewing gum composition, a solution of the stain removing agents is preferably, alternately applied with the flavoring agent.

The sweetener may be present in an amount of from about 30% to 80% by weight of the coating syrup. A binder such as magnesium stearate may be added to the coating syrup in an amount of from about 1% to 15% by weight of the coating syrup to enhance or promote adhesion. Optionally, minor amounts of conventional additives may also be present. The sweeteners suitable for use in the coating syrup comprise sugarless sweeteners such as the polyhydric alcohols, e.g., xylitol, sorbitol, mannitol, and mixtures, thereof; as well as maltitol, isomaltitol, hydrogenated starch hydrolysates, and hydrogenated glucose syrups. Mono, di- and polysaccharide may also be included. For example, sugars such as sucrose, fructose, glucose, galatose and maltose may also be employed as a sweetener. Other sweeteners suitable for use in the coating syrup include, but are not limited to free saccharin acid, water soluble salts of saccharin, cyclamate salts, palatinit dihydrochalcones, glycyrrhizin, L-aspartyl-L-phenylalanine methyl ester, amino acid based sweeteners, talin, steviosides, dihydrochalcone compounds, acesulfame salts and mixtures thereof.

Other ingredients may be added in minor amounts to the coating syrup and include moisture absorbing compounds, anti-adherent compounds, dispersing agents and film forming agents. The moisture absorbing compounds suitable for use in the coating syrups include mannitol or dicalcium phosphate. Examples of useful anti-adherent compounds, which may also function as filler, include talc, magnesium trisilicate and calcium carbonate. These ingredients may be employed in amounts of about 0.5% to 5% by weight of the syrup. Examples of dispersing agents, which may be employed in the coating syrup, include titanium dioxide, talc or other anti-adherent compounds as set forth above.

The coating syrup is usually heated and a portion thereof deposited on the cores. Usually a single deposition of the coating syrup is not sufficient to provide the desired amount or thickness of coating and it usually will be necessary to apply second, third or more coats of the coating syrup in order to build up the weight and thickness of the coating to desired levels with layers allowed to dry in-between coats.

A preferred aspect of the chewing gum composition of the present invention comprises adding the stain removing agents to the coating. The stain removing agents are preferably applied subsequent to the syrup coating. It is preferred to then apply a coating of high intensity sweetener prior to coating with the portion containing the stain removing agents. The coating containing the stain removing agents is preferably applied alternately to the application of a flavorant solution. In the practice of the present invention, the coating containing the stain removing agents may be applied as a solution or may be applied as a dry charge or, where applicable, melted and applied. For fatty acid salts, a dry charge may be preferred. In coating a chewing gum composition, the applications of coating syrup are continued until the average gum piece weight reaches the required coating weight, preferably until the coating comprises from about 20% to 30% by weight of the final pellet weight. Further details regarding the preparation of chewing gum compositions can be found in Skuse's Complete Confectioner (13$^{th}$ Edition) (1957) including pp. 41–71, 133–144, and 255–262; and Sugar Confectionery Manufacture (2$^{nd}$ Edition) (1995), E. B. Jackson, Editor, pp. 258–286, the content of which is incorporated herein by reference.

The present invention also encompasses confectionery compositions containing a suitable selection of the present combination of stain removing agents. Confectionery compositions include compressed tablets such as mints, hard boiled candies, nougats, gels, centerfill confections, fondants, panning goods and other compositions falling within the generally accepted definition of confectionery compositions.

Confectionery compositions in the form of pressed tablets such as mints may generally be made by combining finely sifted sugar or sugar substitute, flavoring agent (e.g. peppermint flavor), bulking agent such as gum arabic, and an optional coloring agent. The flavoring agent and the bulking agent are combined and then gradually the sugar or sugar substitute are added along with a coloring agent, if needed.

The product is then granulated by passing through a sieve of desired mesh size (e.g. 12 mesh) and then dried at typically 55° C. to 60° C. The resulting powder is fed into a tableting machine fitted with a large size punch and the resulting pellets are broken into granules and then pressed.

High boiled candies typically contain sugar or sugar substitute, glucose, water, flavoring agent and optional coloring agent. The sugar is dissolved in the water and glucose is then added. The mixture is brought to a boil. The resulting liquid to which may previously have been added a coloring agent is poured onto an oiled slab and cooled. The flavoring agent is then added and kneaded into the cooled mass. The resulting mixture is then fed to a drop roller assembly known in the art to form the final hard candy shape.

A nougat composition typically includes two principal ingredients, a high boiled candy and a frappe. By way of example, egg albumen or substitute thereof is combined with water and whisked to form a light foam. Sugar and glucose are added to water and boiled typically at about 130° C. to 140° C. and the resulting boiled product is poured into a mixing machine and beat until creamy. The beaten albumen and flavoring agent are combined with the creamy product and the combination is thereafter thoroughly mixed.

Further details regarding the preparation of confectionery compositions can be found in Skuse's Complete Confectioner (13$^{th}$ Edition) (1957) including pp. 41–71, 133–144, and 255–262; and Sugar Confectionery Manufacture (2$^{nd}$ Edition) (1995), E. B. Jackson, Editor, pp. 129–168, 169–188, 189–216, 218–234, and 236–258, the content of which is incorporated herein by reference.

In another embodiment of the present invention, there is provided a method of removing stains from dental surfaces of the oral cavity in warm-blooded animals including humans, by administering, applying or contacting a stain removing effective amount of the compositions of the present invention including chewing gum and confectionery compositions to the oral cavity. The stain removing effective amount of the compositions of the present invention is preferably administered, applied or contacted to the surface of the teeth, for the treatment or prevention of stains on dental surfaces, in one or more conventional ways. For example, the dental surfaces may be rinsed with a solution (e.g., mouthwash, rinse) containing the composition of the present invention. If a dentifrice (e.g., toothpaste, tooth gel, or tooth powder) is employed, the teeth may be bathed in the liquid and/or lather generated by brushing the teeth, etc., for a sufficient time, preferably from about 10 seconds to 10 minutes, more preferably from about 30 seconds to 60 seconds. The method of the present invention may further involve expectoration of most of the composition following contact of the present composition to the dental surfaces.

The frequency of the application or contact of the composition to the dental surfaces is preferably from about once a week to about four times per day, more preferably from about 3 times per week to three times per day, even more preferably at least once per day. The period of such treatment typically ranges from about one day to a lifetime. For particular stains the duration of stain removing treatment depends on the severity of the stain being treated, the particular delivery form utilized and the warm-blooded animal's response to treatment.

Other non-limiting examples include administering, applying or contacting the compositions of the present invention to the teeth include rinsing with a mouthwash or rinse solution and brushing with a dentifrice. Other methods of applying the present composition to the surfaces of the teeth are apparent to those skilled in the art. Preferred methods of applying the chewing gum and confectionery compositions include chewing gum that contains the composition of the present invention, chewing or sucking on a breath tablet or lozenge or other confectioneries.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

EXAMPLE 1

Experimental Results from a Stain Removal Study

Materials and Methods

A flow system was prepared to treat hydroxyapatite (HAP) disks for staining. Tea, coffee and porcine gastric mucin solution was mixed to yield a staining broth. The staining broth was circulated through the flow system in contact with the HAP disks at a rate of 15 ml per minute for about 96 hours at 37° C. The resulting stained HAP disks were rinsed in a solution of artificial saliva at a pH of about 7 and allowed to dry for about 2 hours at room temperature.

Once the HAP disks were dry, a baseline stain reading was determined for each HAP disk by measuring its diffuse reflectance absorbance value using a Minolta spectrometer. The measurement was made over the entire visible color spectrum in accordance with the Commission International de L'Eclairage Laboratory (CIELAB) color scale. The CIELAB color scale quantifies color according to 3 parameters: lightness-darkness scale (L), red-green chroma (RGC), and yellow-blue chroma (YBC). An average of three absorbance measurements were made for each HAP disk. The HAP disks were then divided into seven balanced groups of five HAP disks each.

Seven test solutions were prepared each containing solutions selected from 0.05% sodium stearate (SS); 0.05% sodium hexametaphosphate (SHMP); 0.05% sodium tripolyphosphate (STPP); 0.05% tetrasodium pyrophosphate (TSPP); 0.05% sodium stearate (SS) and 0.05% sodium hexametaphosphate (SHMP); 0.05% sodium stearate (SS) and 0.05% sodium tripolyphosphate (STPP); and 0.05% sodium stearate (SS) and 0.05% tetrasodium pyrophosphate (TSPP).

Results

Each group of stained HAP disks was treated with a corresponding test solution for comparative examination of their stain removing activity. No control test solution was used in this study. The HAP disks were placed in the flow system and treated with the corresponding test solution at a flow rate of about 15 ml/min for about one hour at 37° C. The treated HAP disks were allowed to air-dry for 2 hours at room temperature. Each of the treated HAP disk was measured for changes in staining color. The overall change in stain level (ΔE) was determined for each of the treated HAP disks. The ΔE value for each test solution is shown in Table 1 below, with greater values indicating less stain and greater whitening of the disks.

TABLE 1

Stain Removal Results Corresponding to Each Test Solution

| Test Solution | ΔE values |
| --- | --- |
| Sodium stearate (0.05%) | 5.7 |
| Sodium hexametaphosphate (0.05%) | 4.3 |
| Sodium tripolyphosphate (0.05%) | 6.8 |
| Tetrasodium pyrophosphate (0.05%) | 3.7 |
| Sodium stearate (0.05%)/ Sodium hexametaphosphate (0.05%) | 9.2 |
| Sodium stearate (0.05%)/ Sodium tripolyphosphate (0.05%) | 10.8 |
| Sodium stearate (0.05%)/ Tetrasodium pyrophosphate (0.05%) | 8.0 |

The results shown in Table 1 as indicated by the ΔE values demonstrate a stain removing effect for all test solutions.

EXAMPLE 2

In-Vitro Stain Removal Study

Materials and Methods

Several hydroxyapatite disks were prepared and pretreated to form on the surface of the disks a biofilm that was discolored with a vegetable stain. The color intensity of each disk was then determined utilizing a Chrom-A-Meter. The disks were suspended in either water or a test solution containing a solution selected from 1) 0.05% sodium stearate; 2) 0.3% sodium tripolyphosphate, 3) 0.3% carbamide peroxide; 4) 0.3% carbamide peroxide and 0.05% sodium stearate; and 5) 0.3% carbamide peroxide and 0.3% sodium tripolyphosphate, respectively. Water acts as a control to take into account the differences in the disk composition and the variation in the stain thickness between batches. The disks were treated for two ten (10) minute intervals, and characterized by the Chrom-A-Meter after each treatment interval. The change in color is expressed by ΔE values relative to the water treatment alone. The percent stain reduction is then calculated. The results are presented in FIG. 1.

Figure 1:
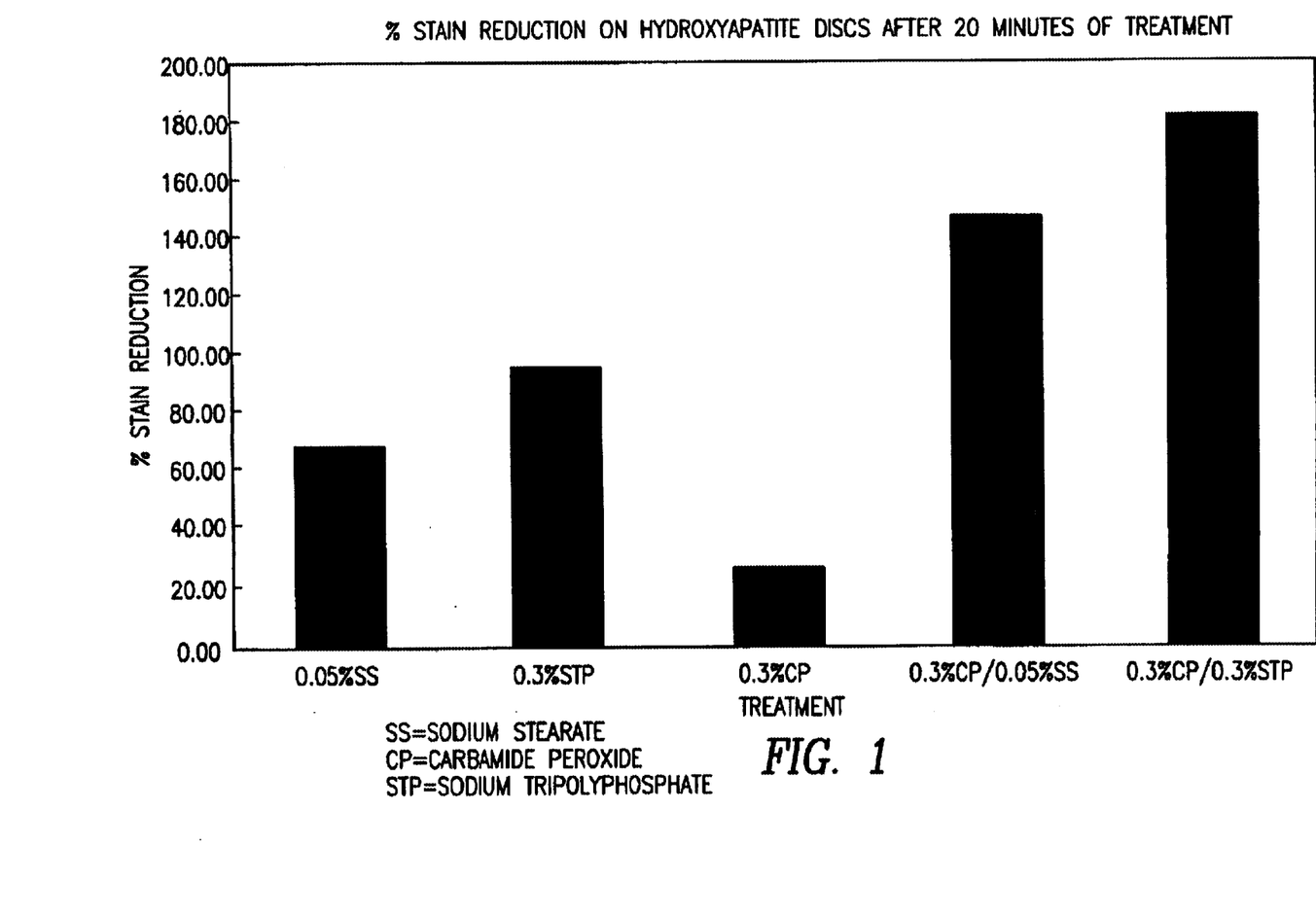
FIG. 1 is a graph showing the % stain reduction obtained from soaking stained hydroxyapatite disks in test solutions in accordance with the present invention.

As shown in FIG. 1, the combination of carbamide peroxide and sodium stearate and the combination of carbamide peroxide and sodium tripolyphosphate enhanced stain removing effect over what would be expected from the results achieved with the individual stain removing components alone.

Preparation of the Stain Solution

The stain solution was comprised of components prepared from coffee (e.g., Chock Full O'Nuts All Method Grind), tea (e.g., Lipton Flo-Thru Tea Bags), blueberry pie filling, and grape juice (e.g., Welch's) and mixed together. 500 mL of coffee, prepared in a coffee maker using 3½ scoops of coffee to 700 mL of water; was placed in a 4-L Erlenmeyer flask and stirred. 50 mL of blueberry pie filling was liquefied and added to the 4-L Erlenmeyer flask, and the contents were stirred. 500 mL of tea, prepared by steeping 4 Lipton Flo-Thru tea bags in 600 mL of pre-boiled water for about 5 minutes in a 800 mL beaker, was added to the 4-L Erlenmeyer flask. Then, 50 mL of the grape juice was added to the flask, and the contents were stirred to form the stain solution.

Staining Procedure

Hydroxyapatite disks were placed with the bottom surface down on the bottom of a glass dish. The disks were maintained in a slightly moist state. The stain solution was poured down the sides of the glass dish avoiding direct flow over the surface of the disks, until the disks were covered by at least ½ inch of the stain solution. The glass dish was covered, and the disks were allowed to soak overnight at room temperature. A beaker was filled with water at 25° C., and each disk was dipped in the water after removal from the stain solution, and placed in a dish lined with an absorbent towel with the stain side up. The disks were allowed to dry overnight at 37° C.

Treatment of Stained Disks

Test solutions were each prepared in 400 g of distilled water along with the corresponding amounts of the active components to achieve the above concentration levels at 37° C. The test solutions were continuously stirred at about 400 rpm. The negative control consisted of 400 g of distilled water at 37° C., which was also continuously stirred at about 400 rpm. Each of the stained disks was checked with the Chrom-A-Meter to determine the CIELAB value. The disks were each picked up with a pair of forceps, and suspended in the corresponding test solution or water (control). Each disk was held between the side of the beaker and the vortex from the stirring midway below the surface of the solution for about 10 minutes. Each disk was then removed from the solution and allowed to dry. Each of the disks was checked by the Chrom-A-Meter to determine the CIELAB value. The above treatment procedure was repeated for each disk for a total of 20 minutes of treatment.

Results

The test results as shown in FIG. 1, indicate that the test solutions containing carbamide peroxide in combination with sodium stearate and sodium tripolyphosphate, respectively, provided a marked reduction in the occurrence of staining after the test period over each of the test solutions containing the individual active ingredients alone and in comparison to treatment with water alone.

EXAMPLE 3

In-Vitro Stain Removal Study

Materials and Methods

Five coated gum samples were tested in a stain removal test model each an active compositions selected from 1) 0.5% sodium stearate in a core portion; 2) 0.5% sodium stearate in a coating portion and 3% carbamide peroxide in a core portion; 3) 0.5% sodium stearate in a coating portion and 1% sodium tripolyphosphate in a core portion; 4) 0.5% sodium stearate in a coating portion and 3% sodium tripolyphosphate/carbamide peroxide in a core portion; and 5) 0.5% sodium stearate in a coating portion and 1% sodium tripolyphosphate/carbamide peroxide in a core portion. The gum samples were masticated by a chewing machine, which was outfitted with stained bovine teeth providing chewing surfaces to simulate the top and bottom teeth in a human mouth. The samples were chewed for five minutes. The bovine teeth were checked with a Chrom-A-Meter before they were outfitted into the machine, and checked again after simulated chewing over a one week period (28 doses). The color change was then determined by calculating the ΔE value. All of the stain was then removed from the bovine tooth samples and read again with the Chrom-A-Meter. The percent stain reduction was then calculated. The results are presented in FIG. 2.

Results

The test results indicate that the gum samples containing carbamide peroxide in combination with sodium stearate and sodium tripolyphosphate provided a marked reduction in stains after the test period.

EXAMPLE 4

Chewing Gum Compositions

TABLE 2

| Ingredient | Composition 1 (% w/w) | Composition 2 (% w/w) | Composition 3 (% w/w) |
|---|---|---|---|
| Gum base | 26.25 | 26.25 | 26.25 |
| Calcium Carbonate | 3.75 | 3.75 | 3.75 |
| Sorbitol | 28.05 | 27.55 | 30.55 |
| Mannitol | 7.50 | 7.50 | 7.50 |
| Maltitol | 21.62 | 21.62 | 21.62 |
| Glycerine | 1.00 | 1.00 | 1.00 |
| Flavorant | 3.15 | 3.15 | 3.15 |
| Gum Arabic | 1.16 | 1.16 | 1.16 |
| Titanium dioxide | 0.17 | 0.17 | 0.17 |
| Wax Candellia | 0.03 | 0.03 | 0.03 |
| Sodium Stearate* | 0.50 | — | — |
| Sodium Tripolyphosphate | 3.00 | 3.00 | 3.00 |
| Sweetener | 0.82 | 0.82 | 0.82 |
| IMWITOR 370 ® | — | 1.00 | 1.00 |
| Carbamide Peroxide | 3.00 | 3.00 | — |
| Total | 100.00 | 100.00 | 100.00 |

*Sodium stearate/sodium palmitate @ 50/50

The chewing gum compositions identified in Table 2 were prepared by conventional methods known in the art. The gum base was heated to sufficiently soften the base without adversely affecting the physical and chemical make up of the base. The molten gum base and the filler were then added to a mixing kettle. The sugar alcohols, glycerin, flavor, high intensity sweetener and stain removing agents of the present invention were added with mixing to obtain a homogenous mixture, with the stain removing agents of the present invention, added last. The mixture was then discharged from the mixing kettle and rolled and scored into a desired piece size by conventional techniques.

EXAMPLE 5

A Stain Removal Test Model

Materials and Methods

Using methods similar to those described in Example 2 with the exception of having the hydroxyapatite disks substituted by bovine teeth, five test solutions were tested in a stain removal test model. The bovine teeth were prepared and pretreated to form a biofilm thereon that was discolored with a vegetable stain. The color intensity of each bovine tooth was then determined utilizing a Chrom-A-Meter. The bovine teeth were suspended in either water (control) or a test solution selected from 1) 0.05% sodium tripolyphosphate/0.1% sodium stearate; 2) 0.1% sodium tripolyphosphate/0.05% sodium stearate; 3) 0.1% sodium tripolyphosphate/0.075% sodium stearate; and 4) 0.1% sodium tripolyphosphate/0.1% carbamide peroxide. Treatment with water provided a control to take into account the differences in the tooth composition and the variation in the stain thickness between batches.

The disks were treated for two ten (10) minute intervals, and characterized by the Chrom-A-Meter after each treatment interval. The change in color is expressed in the determination of AE values relative to the water treatment. The percent stain reduction was then calculated from the AE values. The results are presented in FIG. 3.

Results

Figure 3:
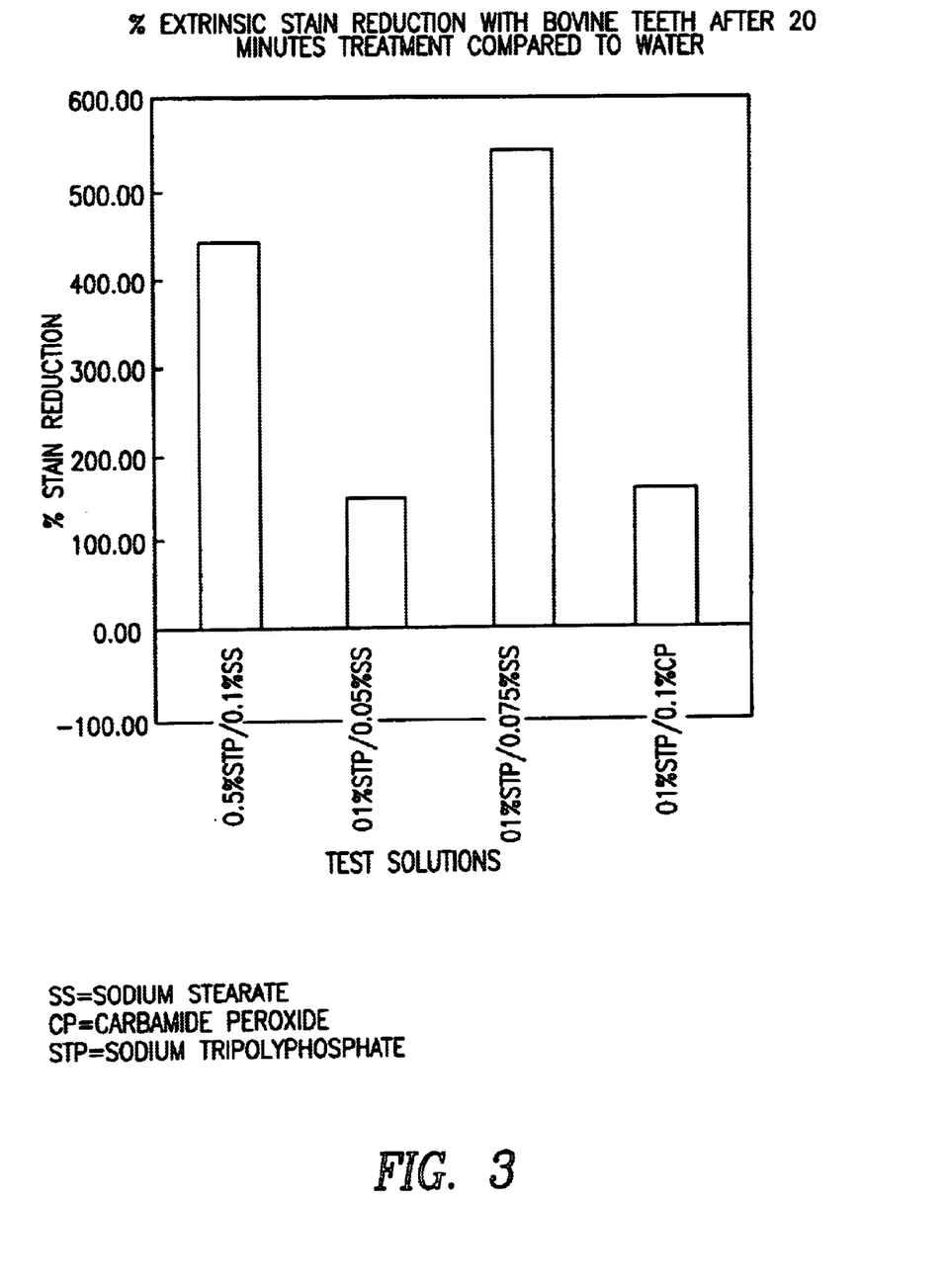
FIG. 3 is a graph showing the % stain reduction obtained from stained bovine teeth after 20 minutes of treatment in test solutions in accordance with the present invention.

As shown in FIG. 3, the test solutions each comprising a particular combination of the staining removing agents of the present invention, exhibited significant stain removing effect as compared to treatment with water alone.

EXAMPLE 6

Pressed Mint Tablet Composition

TABLE 3

| Ingredient | Composition 1 (% w/w) | Composition 2 (% w/w) |
| --- | --- | --- |
| Sorbitol | 90.55 | 85.55 |
| High Intensity Sweetener | 0.15 | 0.15 |
| Flavoring agent | 1.300 | 1.300 |
| Sodium Tripolyphosphate | 3.00 | 3.00 |
| Sodium Stearate* | 5.0 | 10.0 |
| Total | 100.00 | 100.00 |

*Sodium stearate/sodium palmitate @ 50/50

The pressed mint tablet compositions identified in Table 3 were prepared by conventional methods as known in the art. The sweeteners were finely sifted and combined. The other ingredients and the stain removing agents were combined and gradually the sweeteners are added. The resulting mixture was then granulated by passing through a sieve of desired mesh size (e.g. 12 mesh) and then dried at typically 55° C to 60° C. The resulting mixture was then fed into a tableting machine fitted with a large size punch and the resulting pellets are broken into granules and then pressed.

EXAMPLE 7

Clinical Study with Pressed Mints

A clinical study was implemented to establish the stain removing activity of the mint compositions of Example 6 in test subjects. The results corresponding to the mint compositions of Example 6 were compared to results obtained in test subjects receiving no treatment (control). 150 subjects were divided into three groups of 50. Two groups of subjects each received a test composition selected from one of the following: the mint composition 1 of Example 6 and the mint composition 2 of Example 6. A third group received no treatment. The test compositions were administered orally and allowed to dissolve in the subjects' mouths, four times per day over an 8-week period. The subjects were evaluated for tooth stain using a modified Lobene Index at baseline on week 4 and on week 8.

The Lobene Index is a visual scale used by dental care professionals to measure tooth staining. The teeth of the subjects were divided into two regions, the body margin and the gingival margin. The regions were evaluated for both intensity of the stain (i.e., darkness) and the extent of the stain (i.e., area) on a scale of 0 to 3 to determine a total tooth score for each subject. The level of stain was measured over time by comparing the total tooth scores, and deriving therefrom a pairwise comparison of p-values for stain reduction. The results of the study are shown in Table 4.

TABLE 4

Pairwise Comparison of p-values for Stain Reduction

| | Mint Composition 1 | Mint Composition 2 |
| --- | --- | --- |
| Control (No Treatment) | <0.001 | <0.001 |
| Mint Composition 1 | — | 0.091 |

Results

The subjects administered with either mint compositions 1 or 2 were found to have significantly less extrinsic tooth stain compared to the stain reduction exhibited by the control group. It was determined that the stain reduction exhibited by the mint compositions 1 and 2 over no treatment was statistically significant at a level corresponding to $p \leq 0.05$. There was no significant difference in stain reduction between the mint composition 1 group and the mint composition 2 group.

What is claimed is:

1. A confectionery composition for removing stains from dental surfaces comprising a stain removing effective amount of a stain removing component consisting essentially of a peroxide compound, a polyphosphate, and an anionic surfactant, said confectionery composition further comprising an orally acceptable confectionery carrier.

2. The composition of claim 1 wherein the peroxide compound is selected from the group consisting of carbamide peroxide, hydrogen peroxide, calcium peroxide, sodium peroxide, strontium peroxide, zinc peroxide, magnesium peroxide and mixtures thereof.

3. The composition of claim 1 wherein the polyphosphate is selected from the group consisting of tripolyphosphates, tetrapolyphosphates, pyrophosphates, hexametaphosphates and mixtures thereof.

4. The composition of claim 3 wherein the polyphosphate is selected from the group consisting of water soluble alkali metal polyphosphates.

5. The composition of claim 4 wherein the polyphosphate is selected from the group consisting of sodium tripolyphosphate, potassium tripolyphosphate, sodium potassium tripolyphosphate, sodium hexametaphosphate, tetrasodium pyrophosphate, sodium acid pyrophosphate and mixtures thereof.

6. The composition of claim 1 wherein the polyphosphate is present in a stain removing effective amount of from about 0.01% to 5% by weight based on the total weight of the composition.

7. The composition of claim 6 wherein the polyphosphate is present in a stain removing effective amount of from about 0.1% to 3% by weight based on the total weight of the composition.

8. The composition of claim 7 wherein the polyphosphate is present in a stain removing effective amount of from about 1.0% to 3% by weight based on the total weight of the composition.

9. The composition of claim 1 where the anionic surfactant is selected from the group consisting of sulfated butyl oleate, medium and long chain fatty acid esters and salts, sodium and potassium salts of stearate and palmitate and methyl and ethyl esters thereof, sodium oleate, salts of fumaric acid, potassium glomate, organic acid esters of mono- and diglycerides, stearyl monoglyceridyl citrate, succistearin, dioctyl sodium sulfosuccinate, glycerol tristearate, lecithin, hydroxylated lecithin, sodium lauryl sulfate, acetylated monoglycerides, succinylated monoglycerides, monoglyceride citrate, ethoxylated monoand diglycerides, sorbitan monostearate, calcium stearyl-2-lactylate, sodium stearyl lactylate, lactylated fatty acid esters of glycerol and propylene glycol, glycerol-lactoesters of $C_8$–$C_{24}$ fatty acids, polyglycerol esters of $C_8$–$C_{24}$ fatty acids, propylene glycol alginate, sucrose $C_8$–$C_{24}$ fatty acid esters, diacetyl tartaric and citric acid esters of mono and diglycerides, triacetin, and mixtures thereof.

10. The composition of claim 1 where the anionic surfactant is selected from the group consisting of sulfated butyl oleate, medium and long chain fatty acid esters and salts, organic acid esters of mono- and diglycerides, ethoxylated mono- and diglycerides, lactylated fatty acid esters of glycerol and propylene glycol, glycerol-lactoesters of $C_8$–$C_{24}$ fatty acids, polyglycerol esters of $C_8$–$C_{24}$ fatty acids, sucrose $C_8$–$C_{24}$ fatty acid esters, diacetyl tartaric and citric acid esters of mono- and diglycerides, and mixtures thereof.

11. The composition of claim 1 wherein the anionic surfactant is selected from the group consisting of sodium stearate, potassium stearate, sodium palmitate, potassium palmitate, sodium oleate, glycerol stearate, glycerol lactate, glycerol stearate lactate, sucrose monostearate, sucrose distearate, sucrose monolaurate, sucrose dilaurate, polyglycerol esters of monostearate, polyglycerol esters of monolaurate, glycerol-lactoesters of $C_{14}$–$C_{20}$ fatty acids, polyglycerol esters of $C_{14}$–$C_{20}$ fatty acids, sucrose $C_{14}$–$C_{20}$ fatty acid esters, and mixtures thereof.

12. The composition of claim 1 where the anionic surfactant is selected from the group consisting of sodium stearate, sodium palmitate, citric acid esters of mono- and diglycerides, lactic acid esters of mono- and diglycerides, and mixtures thereof.

13. The composition of claim 1 in the form of a chewing gum, said anionic surfactant being present in an amount of from about 0.1% to 2.0% by weight based on the total weight of the composition.

14. The composition of claim 13 wherein the amount of the anionic surfactant is from about 0.4% to 1.2% by weight based on the total weight of the composition.

15. The composition of claim 1 in the form of a confectionery, said anionic surfactant being present in an amount of from about 0.1% to 20% by weight based on the total weight of the composition.

16. The composition of claim 15 wherein the amount of the anionic surfactant is from about 3% to 15% by weight based on the total weight of the composition.

17. The composition of claim 1 wherein the confectionery composition is selected from the group consisting of chewing gums, centerfill confections, nougats, candies, panning goods, gel confections, fondants, lozenges, hard boiled candies, mints, troches, pastilles, microcapsules, cakes, wafers, thin films, tablets and compressed tablets.

18. The composition of claim 1 wherein the peroxide compound is present in a stain removing effective amount of from about 0.01% to 10% by weight based on the total weight of the composition.

19. The composition of claim 18 wherein the peroxide compound is present in a stain removing effective amount of from about 0.1% to 5% by weight based on the total weight of the composition.

20. The composition of claim 19 wherein the peroxide compound is present in a stain removing effective amount of from about 0.2% to 3% by weight based on the total weight of the composition.

21. The composition of claim 1 in the form of a chewing gum, wherein:

the peroxide compound is present in the stain removing effective amount of from about 0.01% to 10% by weight based on the total weight of the composition; and the polyphosphate is present in the stain removing effective amount of from about 0.01% to 5% by weight based on the total weight of the composition.

22. The composition of claim 1 in the form of a chewing gum, wherein:

the peroxide compound is present in the stain removing effective amount of from about 0.01% to 10% by weight based on the total weight of the composition; and the anionic surfactant is present in the stain removing effective amount of from about 0.01% to 2.0% by weight based on the total weight of the composition.

23. The composition of claim 1 in the form of a chewing gum, wherein:

the polyphosphate is present in the stain removing effective amount of from about 0.01% to 5% by weight based on the total weight of the composition; and the anionic surfactant is present in the stain removing effective amount of from about 0.1% to 2.0% by weight based on the total weight of the composition.

24. The composition of claim 1 in the form of a confectionery, wherein:

the peroxide compound is present in the stain removing effective amount of from about 0.01% to 10% by weight based on the total weight of the composition; and the polyphosphate is present in the stain removing effective amount of from about 0.01% to 5% by weight based on the total weight of the composition.

25. The composition of claim 1 in the form of a confectionery, wherein:

the polyphosphate is present in the stain removing effective amount of from about 0.01% to 5% by weight based on the total weight of the composition; and the anionic surfactant is present in the stain removing effective amount of from about 0.1% to 20.0% by weight based on the total weight of the composition.

26. The composition of claim 1 in the form of a confectionery, wherein:

the peroxide compound is present in the stain removing effective amount of from about 0.01% to 10% by weight based on the total weight of the composition; and the anionic surfactant is present in the stain removing effective amount of from about 0.1% to 20.0% by weight based on the total weight of the composition.

27. The composition of claim 1 further comprising an encapsulating substance for encapsulating the peroxide compound within the composition.

28. The composition of claim 27 wherein the encapsulating substance is selected from the group consisting of natural gums, synthetic gums, edible oils, polymers, olefin copolymers, resins, waxes, mineral oils, and mixtures thereof.

29. The composition of claim 1 wherein the orally acceptable confectionery carrier is a solid carrier.

30. The composition of claim 1 wherein the orally acceptable confectionery carrier is a chewing gum or wax base.

31. A method of removing stains from dental surfaces comprising administering a stain removing effective amount of the confectionery composition of claim 1 to the oral cavity of a warm-blooded animal including humans for contact with the dental surfaces thereof.

* * * * *

UNITED STATES PATENT AND TRADEMARK OFFICE
CERTIFICATE OF CORRECTION

PATENT NO. : 6,685,916 B1
APPLICATION NO. : 10/285217
DATED : February 3, 2004
INVENTOR(S) : Samantha K. Holme et al.

Figure 2:
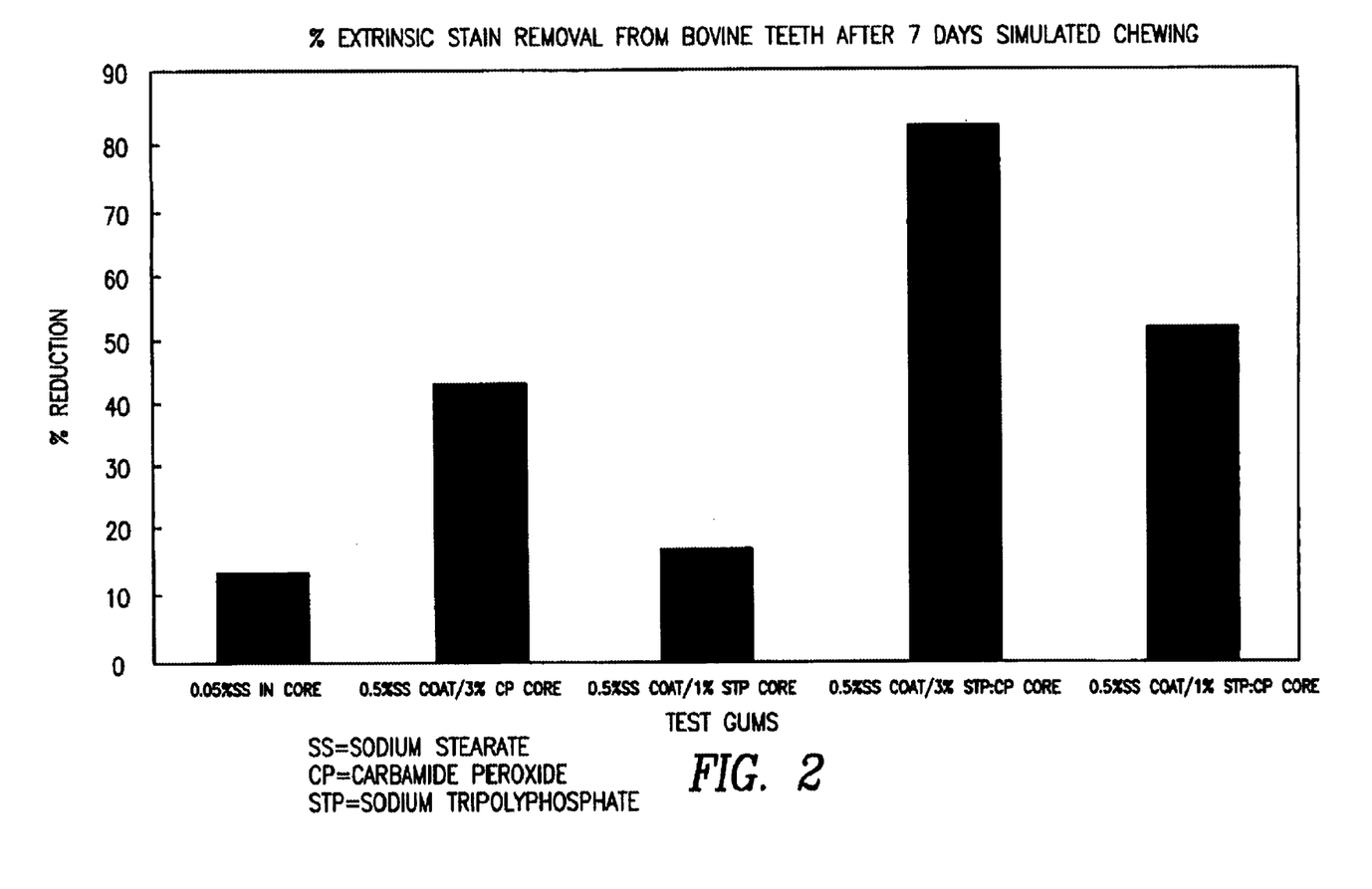
FIG. 2 is a graph showing the % stain reduction obtained from simulated chewing tests utilizing different combinations of stain removing agents incorporated into chewing gum in accordance with the present invention.

It is certified that error appears in the above-identified patent and that said Letters Patent is hereby corrected as shown below:

Figure 2, left hand vertical column, "0.05%SS" should read --0.5% SS--;

Figure 3, first column ", 0.5%STP/0.1%SS" should read --0.05%STP/0.1%SS; and

Figure 3, second, third and fourth vertical columns "01%STP" in each column should read --0.1%STP--.

Signed and Sealed this

Twentieth Day of May, 2008

JON W. DUDAS
*Director of the United States Patent and Trademark Office*